(12) United States Patent
Straaijer et al.

(10) Patent No.: US 7,839,506 B2
(45) Date of Patent: Nov. 23, 2010

(54) INSPECTION METHOD AND APPARATUS, LITHOGRAPHIC APPARATUS, LITHOGRAPHIC PROCESSING CELL AND DEVICE MANUFACTURING METHOD

(75) Inventors: Alexander Straaijer, Eindhoven (NL); Ronald Franciscus Herman Hugers, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 12/718,599

(22) Filed: Mar. 5, 2010

(65) Prior Publication Data

US 2010/0157299 A1    Jun. 24, 2010

Related U.S. Application Data

(62) Division of application No. 11/708,678, filed on Feb. 21, 2007, now Pat. No. 7,701,577.

(51) Int. Cl.
*G01J 4/00* (2006.01)
(52) U.S. Cl. ..................................... 356/369
(58) Field of Classification Search ............... 356/364, 356/369
See application file for complete search history.

(56) References Cited

U.S. PATENT DOCUMENTS

| 4,723,315 | A | * | 2/1988 | Wetherell .................. 398/203 |
| 5,412,473 | A | * | 5/1995 | Rosencwaig et al. ........ 356/451 |
| 5,703,692 | A | | 12/1997 | McNeil et al. |
| 5,880,838 | A | | 3/1999 | Marx et al. |
| 5,963,329 | A | | 10/1999 | Conrad et al. |
| 6,608,690 | B2 | | 8/2003 | Niu et al. |
| 6,699,624 | B2 | | 3/2004 | Niu et al. |
| 6,704,661 | B1 | | 3/2004 | Opsal et al. |
| 6,721,691 | B2 | | 4/2004 | Bao et al. |
| 6,738,138 | B2 | | 5/2004 | Wei |
| 6,753,961 | B1 | | 6/2004 | Norton et al. |
| 6,768,983 | B1 | | 7/2004 | Jakatdar et al. |
| 6,772,084 | B2 | | 8/2004 | Bischoff et al. |
| 6,785,638 | B2 | | 8/2004 | Niu et al. |
| 6,813,034 | B2 | | 11/2004 | Rosencwaig et al. |
| 6,819,426 | B2 | | 11/2004 | Sezginer et al. |
| 6,856,408 | B2 | | 2/2005 | Raymond |
| 6,919,964 | B2 | | 7/2005 | Chu |
| 6,928,628 | B2 | | 8/2005 | Seligson et al. |
| 6,972,852 | B2 | | 12/2005 | Opsal et al. |
| 6,974,962 | B2 | | 12/2005 | Brill et al. |
| 6,987,572 | B2 | | 1/2006 | Lakkapragada et al. |
| 7,046,376 | B2 | | 5/2006 | Sezginer |
| 7,061,615 | B1 | | 6/2006 | Lowe-Webb |

(Continued)

FOREIGN PATENT DOCUMENTS

EP    1 628 164 A2    2/2006

*Primary Examiner*—Roy Punnoose
(74) *Attorney, Agent, or Firm*—Sterne, Kessler, Goldstein & Fox P.L.L.C.

(57) ABSTRACT

The simultaneous measurement of four separately polarized beams upon diffraction from a substrate is used to determine properties of the substrate. Circularly or elliptically polarized light sources are passed via up to three polarizing elements. This polarizes the light sources by 0, 45, 90 and 135°. The plurality of polarizing beamsplitters replaces the use of a phase modulator, but enables the measurement of the intensity of all four beams and thus the measurement of the phase modulation and amplitude of the combined beams to give the features of the substrate.

8 Claims, 8 Drawing Sheets

U.S. PATENT DOCUMENTS

| | | |
|---|---|---|
| 7,061,623 B2 | 6/2006 | Davidson |
| 7,061,627 B2 | 6/2006 | Opsal et al. |
| 7,068,363 B2 | 6/2006 | Bevis et al. |
| 7,369,233 B2 * | 5/2008 | Nikoonahad et al. ........ 356/369 |
| 7,388,668 B2 * | 6/2008 | Potma et al. ................ 356/451 |
| 7,701,577 B2 | 4/2010 | Straaijer et al. |
| 2004/0119970 A1 | 6/2004 | Dusa et al. |
| 2006/0033921 A1 | 2/2006 | Den Boef et al. |
| 2006/0066855 A1 | 3/2006 | Den Boef et al. |
| 2006/0126074 A1 | 6/2006 | Van Der Werf et al. |
| 2006/0139592 A1 | 6/2006 | Den Boef et al. |
| 2008/0198380 A1 * | 8/2008 | Straaijer et al. ............. 356/369 |

* cited by examiner

PRIOR ART

INSPECTION METHOD AND APPARATUS, LITHOGRAPHIC APPARATUS, LITHOGRAPHIC PROCESSING CELL AND DEVICE MANUFACTURING METHOD

CROSS REFERENCE TO RELATED APPLICATIONS

This application is a Divisional of U.S. patent application Ser. No. 11/708,678, filed Feb. 21, 2007 (U.S. Pat. No. 7,701,577), which is incorporated by reference herein in its entirety.

FIELD

The present invention relates to inspection methods usable, for example, in the manufacture of devices by lithographic techniques and to device manufacturing methods using lithographic techniques.

BACKGROUND

A lithographic apparatus is a machine that applies a desired pattern onto a substrate, usually onto a target portion of the substrate.-A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer).—Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at once, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Figure 4:
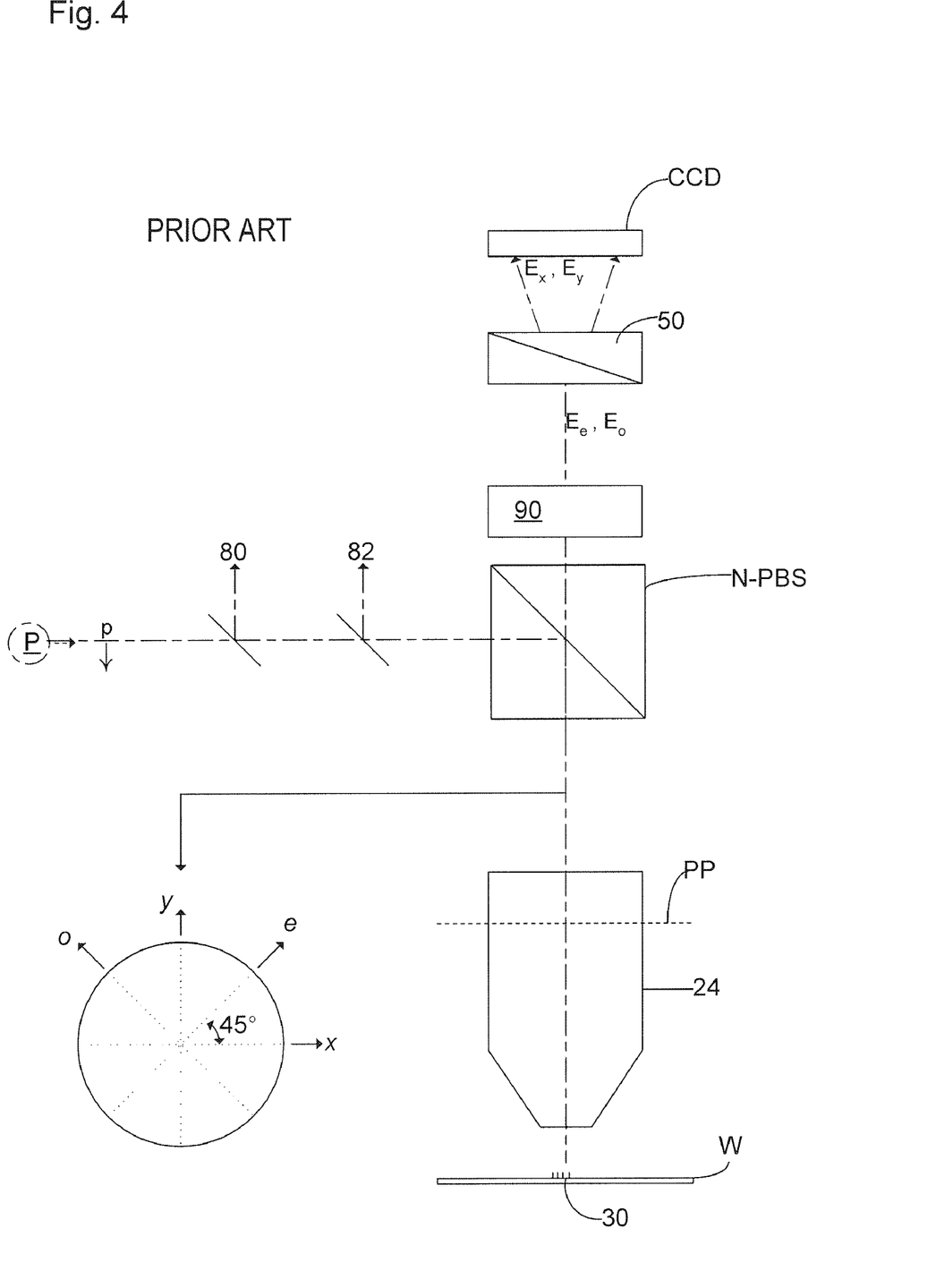
FIG. 4 depicts a conventional inspection apparatus.

The prior art describes an ellipsometric system that enables certain parameters of orthogonally polarized beams to be measured. FIG. 4 shows an example of an ellipsometric sensor (or an ellipsometer) based on the prior art. Illumination radiation from source P is reflected from a structure 30 on a target portion of a substrate W and on its return journey from the substrate, it is linearly polarized along one of the two eigen-polarizations of three beamsplitters that are present in the sensor (the eigen-polarizations being with respect to the x or y direction as shown in FIG. 4). A first beamsplitter 80 sends part of the illumination to an imaging branch; a second beamsplitter 82 sends part of the illumination to a focus branch and a third beamsplitter N-PBS is a non-polarizing beamsplitter that directs part of the beam to a camera CCD. Having passed through the non-polarizing beamsplitter N-PBS, the polarized beam passes through a phase modulator 90 where its ordinary and extraordinary axis have been positioned at 45° with respect to the x and y directions. Subsequently, the beam is divided into its respective x- and y-polarization orientations using a Wollaston prism 50 and impinges on a camera CCD. The relative intensities of the polarized beams are used to determine the relative polarization orientations of the different parts of the beam. From the relative polarization orientations, the effect of the structure 30 on the beam can be determined. From the effect the structure 30 has on the beam, the properties of the structure itself can be determined.

U.S. Pat. No. 5,880,838 (Marx et al.), hereby incorporated in its entirety by reference, also describes the measurement of a structure on a substrate using ellipsometry, wherein the measurement system is called polarization quadrature measurement (PQM). This document describes focusing a polarized beam of light (with TE and TM fields) onto the structure. The TM and TE fields are affected differently by the diffraction off the structure. The TE field can be used as a reference to analyze the phase and amplitude changes in the TM field. The relationship between phases and amplitudes of the TE and TM fields is dependent on the structural parameters (e.g. the depth of a hole or the height of a grating bar or the pitch of a grating) of the structure. By measuring this relationship, therefore, the structural parameters may be determined.

Generally, ellipsometry is the measurement of the state of polarization of scattered light. Ellipsometry measures two parameters: the phase difference ($\Delta$) between two differently polarized beams and an amplitude ratio ($\tan \psi$) of two polarized beams. With these two parameters, any polarization state of a purely polarized beam may be described.

Specifically, if an incident beam has both s and p polarizations, the reflected beam will have reflectance coefficients $R_p$ and $R_s$. The complex amplitudes of each polarization direction are represented by $E_p$ and $E_s$ and are calculated as $R_p \cdot p$ and $R_s \cdot s$, respectively (the Imaginary parts of the complex amplitude being ignorable when only the reflected beam is considered).

$\Delta$ (Delta) is the phase difference between the complex amplitudes $E_p$ and $E_s$ as given in equation (1) below.

The intensity of the received beam is proportional to the sum of the amplitudes, taking into account the angle of their relative polarization. For example, if the polarizations of both $E_p$ and $E_s$ are aligned in the same orientation, the intensity of the received beam is at a maximum. If the two amplitudes are in orthogonal orientations, they cancel each other out and the intensity is at a minimum. The angle between the two polarization directions (or orientations) is $\psi$ and so the relationship between $\psi$ and $E_p$ and $E_s$ is as follows in equation (2).

$$\Delta = \arg(E_p - E_s) \quad (1)$$

$$\tan \psi = E_p / E_s \quad (2)$$

where $$E_p = R_p \cdot p \quad (3)$$

$$E_s = R_s \cdot s \quad (4)$$

Figure 5:
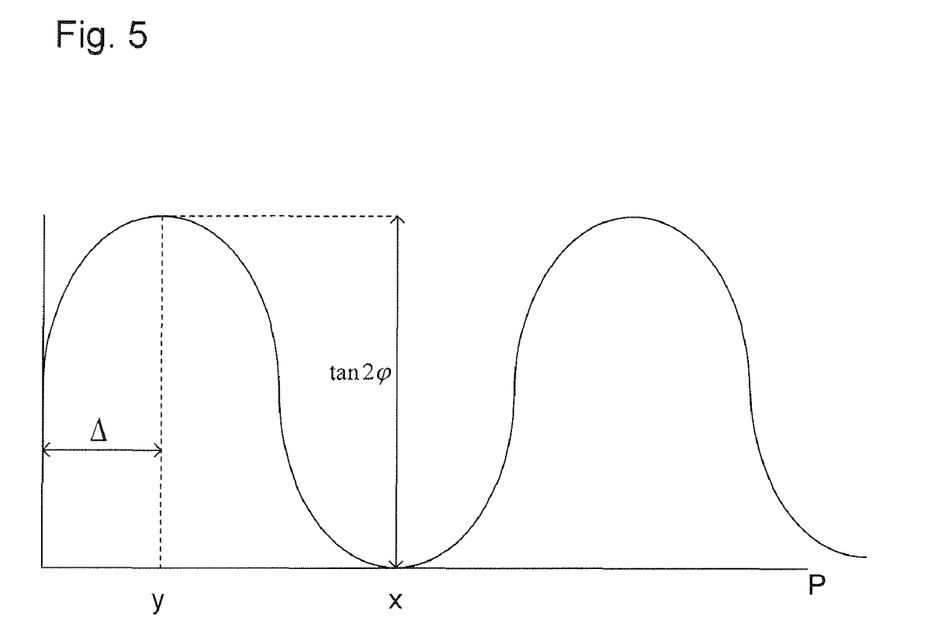
FIG. 5 depicts the relationship between intensity and polarization of a beam reflected from a structure.

FIG. 5 shows the relationship between these two parameters. Specifically,

FIG. 5 shows the intensity variation in one pixel as a function of phase difference between s and p that is imposed by the phase modulator. I is the intensity of the beam and P is the overall polarization of $E_p$ and $E_s$. Assuming the two amplitudes are the same (i.e. $E_p = E_s$ and $\psi = 45°$), the intensity of the overall beam is at a minimum at point x because the polarization directions cancel each other out. At point y, the intensity is at a maximum, indicating that the polarization directions are aligned.

The overall intensity shown in FIG. 5 is modulated, demonstrating that the amplitudes (being the same) cancel each other out to a greater or lesser extent and so the relative phase of the two beams can be monitored as changing accordingly (as dictated by the phase modulator).

The problem with a system such as that shown in FIG. 4 that incorporates a phase modulator is that phase modulators (or phase shifters) have specific disadvantages as listed below.

1. The phase shifts that are applied to the light need to be known exactly because any inaccuracies in these phase shifts will result in the same inaccuracy in A. The relationship between intensity and phase must be clear in order for the structure to be accurately determined.

2. Phase modulators are wavelength-dependent, which means that phase modulators have to be recalibrated for each wavelength that is used.

3. With phase modulators, two or more phase shifts are applied to each beam of light at a specific wavelength. The intensities of the differently shifted beams have to be re-measured for each shift, taking significant amounts of time.

SUMMARY

It is desirable to provide an ellipsometric function in a scatterometer such that phase difference and amplitude of a beam diffracted from a structure may be measured without the disadvantages of known phase modulators with ranges of wavelengths.

According to an embodiment of the invention, there is provided an inspection apparatus, lithographic apparatus or lithographic cell configured to measure a property of a substrate, including: a light source configured to supply a radiation beam; an optical element configured to focus the radiation beam onto a substrate; a polarizing device configured to polarize at least four portions of the radiation beam into four different polarization orientations; and a detector system configured to detect simultaneously an angle-resolved spectrum of the four polarization orientations of the radiation beam.

According to an embodiment of the invention, there is provided an inspection apparatus, a lithographic apparatus or a lithographic cell configured to measure a property of a substrate, the inspection apparatus, lithographic apparatus or lithographic cell including: a light source configured to supply a radiation beam; an optical element configured to focus the radiation beam onto a substrate; a beamsplitter configured to separate the radiation beam once reflected from the surface of the substrate into first and second sub-beams; a first polarizing beamsplitter configured to split the first sub-beam into two orthogonally polarized sub-sub-beams; a second polarizing beamsplitter configured to split the second sub-beam into two further orthogonally polarized sub-sub-beams; and a detector system configured to detect simultaneously an angle-resolved spectrum of the four sub-sub-beams reflected from a surface of the substrate.

According to an embodiment of the invention, there is provided an inspection apparatus, a lithographic apparatus or a lithographic cell configured to measure a property of a substrate, the inspection apparatus, lithographic apparatus or lithographic cell including: a light source configured to supply a radiation beam; an optical element configured to focus the radiation beam onto a substrate; a beamsplitter configured to separate the radiation beam once reflected from the surface of the substrate into first and second orthogonally polarized sub-beams; a first polarizing beamsplitter configured to split the first sub-beam into two sub-sub-beams with about 0 and 90 degree polarization respectively; a second polarizing beamsplitter rotated by about 45 degrees with respect to the first polarizing beamsplitter and configured to split the second sub-beam into two sub-sub-beams with about 45 and about 135 degree polarization respectively; and a detector system configured to detect simultaneously an angle-resolved spectrum of the four sub-sub-beams reflected from a surface of the substrate.

According to an embodiment of the present invention, there is provided a method of measuring a property of a substrate, the method including: providing a radiation beam with elliptical polarization; reflecting the radiation beam off the surface of a substrate; splitting the reflected radiation beam into first and second orthogonally polarized sub-beams; splitting the first sub-beam into first and second sub-sub-beams with polarizations of about 0 and about 90 degrees respectively; splitting the second sub-beam into third and fourth sub-sub-beams with polarizations of about 45 and about 135 degrees respectively; and simultaneously detecting all four sub-sub-beams.

According to an embodiment of the present invention, there is provided an inspection apparatus, a lithographic apparatus or a lithographic cell configured to measure a property of a substrate, the inspection apparatus, lithographic apparatus or lithographic cell including: a light source configured to supply a radiation beam; an optical element configured to focus the radiation beam onto a substrate; a beamsplitter configured to separate the radiation beam once reflected from the surface of the substrate into first and second orthogonally polarized sub-beams; a first polarizing beamsplitter configured to split the first sub-beam into two sub-sub-beams with a phase shift of about 0 and about 180 degree respectively using polarizer orientations of about 0 and 90 degrees; a half wave plate oriented at about 22.5 degrees configured to rotate the polarization of the second sub-beam by about 45 degrees; a second polarizing beamsplitter configured to split the second sub-beam into two sub-sub-beams with phase shifts of about 0 and about 180 degrees respectively using polarizers with an orientation of about 45 and about 135 degrees respectively; and a detector system configured to detect simultaneously an angle-resolved spectrum of the four sub-sub-beams reflected from a surface of the substrate.

According to an embodiment of the invention, there is provided a method of measuring a property of a substrate, the method including: providing a radiation beam with circular polarization; reflecting the radiation beam off the surface of a substrate; splitting the reflected radiation beam into first and second orthogonally polarized sub-beams; splitting the first sub-beam into first and second sub-sub-beams with phase shifts of about 0 and 180 degrees respectively using polarizers with orientations of about 0 and 90 degrees respectively;

rotating the polarization of the second sub-beam by about 90 degrees; splitting the second sub-beam into third and fourth sub-sub-beams with phase shifts of about 0 and 180 degrees respectively using polarizers oriented at about 45 and 135 degrees respectively; and simultaneously detecting all four sub-sub-beams.

According to an embodiment of the present invention, there is provided an inspection apparatus, a lithographic apparatus or a lithographic cell configured to measure a property of a substrate, the inspection apparatus, lithographic apparatus or lithographic cell including: a light source configured to supply a radiation beam; an optical element configured to focus the radiation beam onto a substrate; an optical splitting element configured to separate the radiation beam once reflected from the surface of the substrate into first, second, third and fourth spatially separated sub-beams; four polarizing devices configured to polarize the first, second, third and fourth sub-beam with about 0, 45, 90 and 135 degree polarization orientations respectively; and a detector system configured to detect simultaneously an angle-resolved spectrum of the four sub-beams reflected from a surface of the substrate.

According to an embodiment of the invention, there is provided a method of measuring a property of a substrate, the method including: providing a radiation beam with circular polarization; reflecting the radiation beam off the surface of a substrate; splitting the reflected radiation beam into four sub-beams; transmitting the four sub-beams through four differently oriented polarizing devices to create four polarized beams with polarization orientations of about 0, 45, 90 and 135 degrees respectively; and simultaneously detecting all four sub-beams.

According to an embodiment of the invention, there is provided an inspection apparatus, a lithographic apparatus or a lithographic cell configured to measure a property of a substrate, the inspection apparatus, lithographic apparatus or lithographic cell including: a light source configured to supply a radiation beam; an optical element configured to focus the radiation beam onto a substrate; a matrix of polarizing devices configured to polarize the radiation beam into a matrix of polarized sub-beams, the matrix including an array of units, each unit having four quadrants with about 0, 45, 90 and 135 degree polarization orientations respectively; and a detector system configured to detect simultaneously an angle-resolved spectrum of all of the polarization orientations of the radiation beam reflected from the surface of the substrate.

According to an embodiment of the present invention, there is provided a method of measuring a property of a substrate, the method including: providing a radiation beam with circular polarization; reflecting the radiation beam off the surface of a substrate; transmitting the radiation beam through a matrix of polarizing devices to create a matrix of polarized sub-beams, the matrix including an array of units, each unit having four quadrants with polarizations of about 0, 45, 90 and 135 degrees respectively; and simultaneously detecting the matrix of sub-beams.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
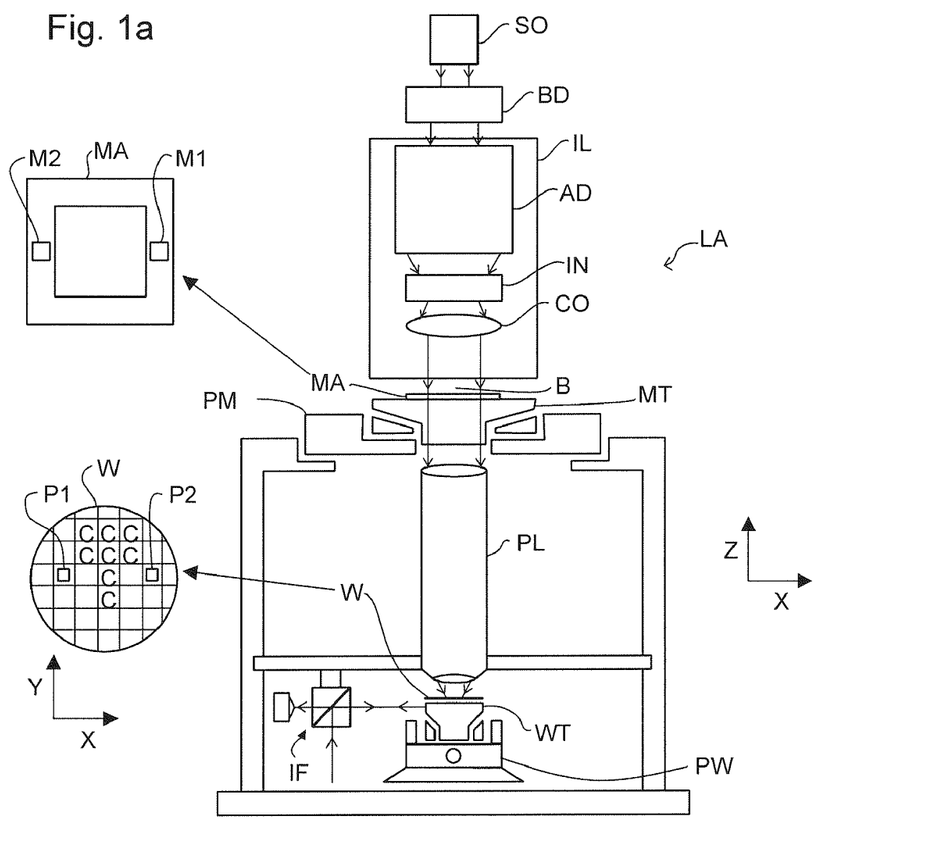
FIG. 1a depicts a lithographic apparatus in accordance with an embodiment of the invention.

FIG. 1a schematically depicts a lithographic apparatus. The apparatus includes: an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is—reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system-".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate.- An immersion liquid may also be applied to other spaces in the lithographic apparatus, for example, between the patterning device (e.g. mask) and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
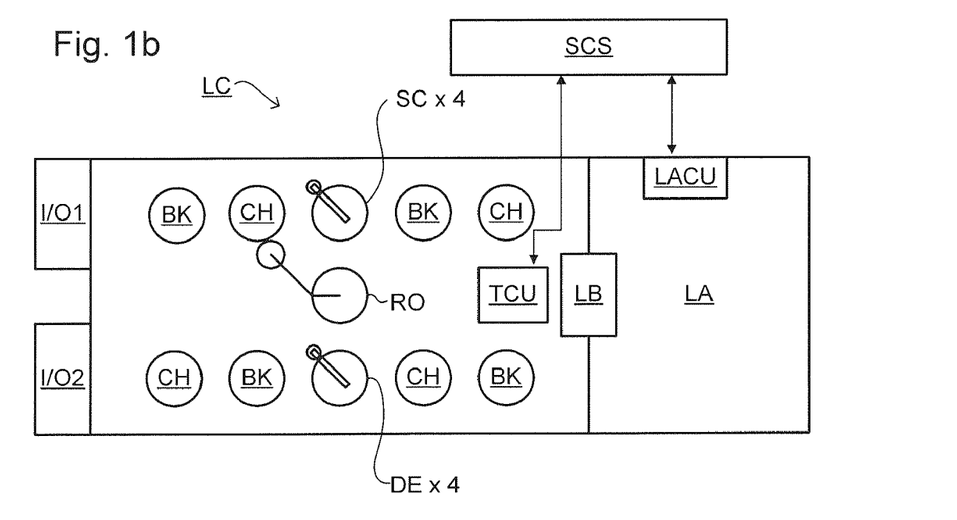
FIG. 1b depicts a lithographic cell or cluster in accordance with an embodiment of the invention.

As shown in FIG. 1b, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 2:
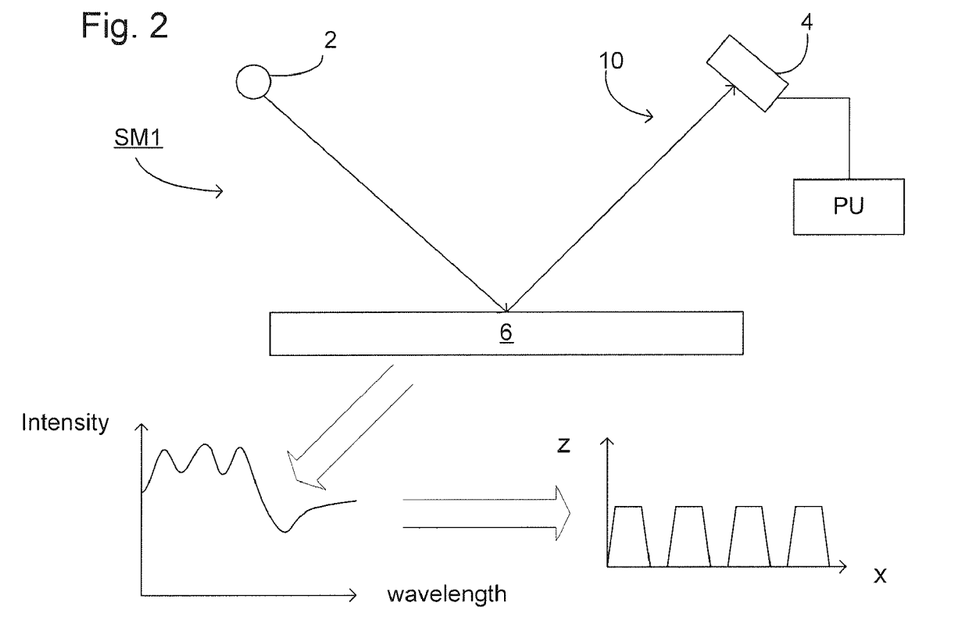
FIG. 2 depicts a scatterometer in accordance with an embodiment of the invention.

FIG. 2 depicts a scatterometer which may be used in an embodiment of the present invention. It includes a broadband (white light) radiation projector 2 which projects radiation onto a substrate 6. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
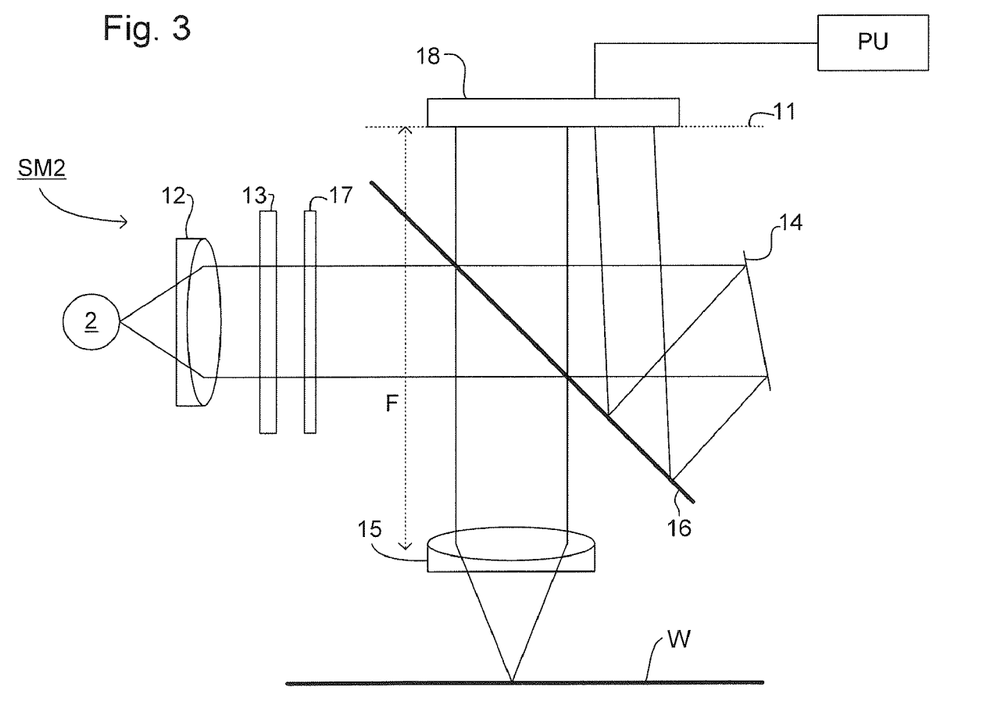
FIG. 3 depicts a scatterometer in accordance with an embodiment of the invention.

Another scatterometer that may be used in an embodiment of the present invention is shown in FIG. 3. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beamsplitter 16 part of it is transmitted through the beamsplitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least $2\delta\lambda$ (i.e. twice the wavelength). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, hereby incorporated in its entirety by reference.

The target on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

As discussed above, an ellipsometer may be used to determine the shapes and other properties of structures on a substrate. The way this is done is that an incident beam is reflected from a substrate W as shown in FIG. 4, this incident beam reflecting off a structure 30. The reflected beam passes through a microscope objective 24, through a non-polarizing beamsplitter N-PBS and through focusing lenses (or other optics) onto a camera CCD.

In the prior art discussed above, the beam is split by a further beamsplitter 50 and directed onto the camera CCD. At this point, the beam is either a TM (transverse magnetic) polarized beam or a TE (transverse electric) polarized beam. Polarization in a TM (or p) direction is parallel to the plane of incidence of the beam and the magnetic (M) field is perpendicular to the plane of incidence. A TE (or s) beam is perpendicular to the plane of incidence and the electric (E) field is parallel to the plane of incidence of the beam. The direction of polarization at the pupil plane PP is shown in FIG. 4.

FIG. 4 also shows a phase modulator 90 positioned between the non-polarizing beamsplitter N-PBS and the beamsplitter 50 that separates the polarized beams prior to transmitting those polarized beams to the camera CCD. An eo-coordinate system that is orientated along the extraordinary and ordinary axes of the phase modulator 90 is also shown in FIG. 4 as a circle and shows a relative position of the extraordinary and the ordinary axes compared to the y and x axes of the system. $E_o$ and $E_e$ are the unknown complex amplitudes of the scattered fields along, respectively, the e and o directions. In this conventional system, it is these amplitudes, compared with the changed phase as predefined by the phase modulator that enables the system to determine the parameters of the structure 30.

In order to remove the phase modulator, several embodiments are envisaged. The feature that the embodiments have in common is that of obtaining four differently polarized reflected sub-beams from a single incident beam in order to measure, from a measured intensity of each sub-beam, the difference in amplitude and phase of the four known polarizations.

Figure 7:
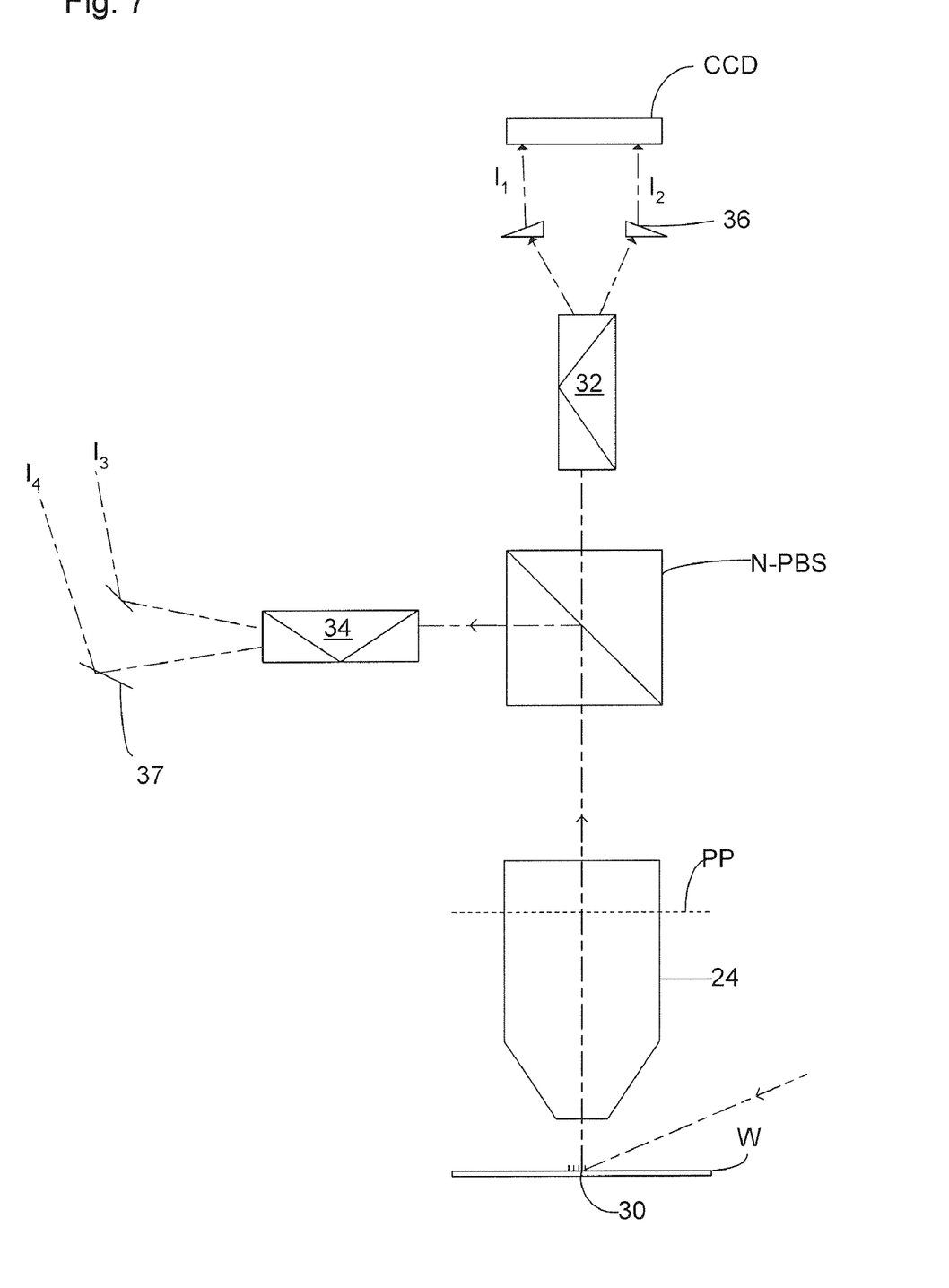
FIG. 7 depicts an ellipsometer according to an embodiment of the present invention.

FIG. 7 shows an ellipsometer in accordance with an embodiment of the invention. A basic set up of a scatterometer such as that shown in FIG. 2 or FIG. 3 is used. A microscope objective 24 receives a beam that is reflected from the structure 30 present on the substrate W. The incident beam may have passed through the microscope objective before reflecting off the structure 30, or it may have been focused using other means. The reflected beam will be measured for reflection from the structure 30 over a range of incident angles (generally 0 to 80°, though of course any possible incident angle is envisaged). The incident beam will also be reflected and measured for all azimuthal angles (0 to)360°. In order to be able to measure a reflected beam for all azimuthal as well as incident angles, the incident beam is circular rather than linear, enabling all directions of polarization and reduced risk of loss of some of the beam during reflection.

The incident light for each measurement is of a fixed wavelength and has a known polarization state. The same wavelength and polarization state will be investigated at multiple angles of incidence (about 0-80°) and at all azimuthal angles (0-360°) as described above. The returning or reflected light beam consists of an infinite number of rays with different polarization states.

Ellipsometry compares the reflectance of p-polarized components with s-polarized components. When using linearly polarized light, on azimuths of 0 and 90°, information from one polarization state will be measurable, but the information from the other polarization state will be missing. Ellipsometry on linearly polarized light therefore works best at around azimuths 45° and 135°. As mentioned above, one way of removing this abnormality is to use circular or elliptical light.

FIG. 7 shows a combined light beam that is elliptically polarized and enters a non-polarizing beamsplitter N-PBS where about 50% of the light will be transmitted and 50% will be deflected (though beamsplitters can be manufactured to transmit and deflect various percentages of incident radiation). The ellipsometric data of the transmitted beam are measured by separating its energy of the x- and y-polarized components $I_1$ and $I_2$ with the help of a polarizing beamsplitter 32 (for instance a Wollaston prism) and a prism 36. This gives rise to the orthogonally polarized sub-beams of the prior art. However, the phase of the polarization needs to be changed in order to be compared to give a full picture of the state of the beam reflected from the structure. To avoid the use of a phase modulator, the other half of the beam that has been divided by the non-polarizing beamsplitter N-PBS is analyzed in a similar way by being separated in a further beamsplitter 34 into sub-sub beams $I_3$ and $I_4$. In order to obtain these further sub-sub-beams that need to have yet different polarizations from $I_1$ and $I_2$, the second beamsplitter 34 is rotated by 45° with respect to the first beamsplitter 32 along its respective longitudinal axis. The beams $I_1$, $I_2$, $I_3$ and $I_4$ are then focused on to a CCD camera. The ellipsometric data, $\Delta$ and tan $\psi$ can be obtained by simple goniometry, which depends on the polarization state of the initial incident beam.

Figure 6:
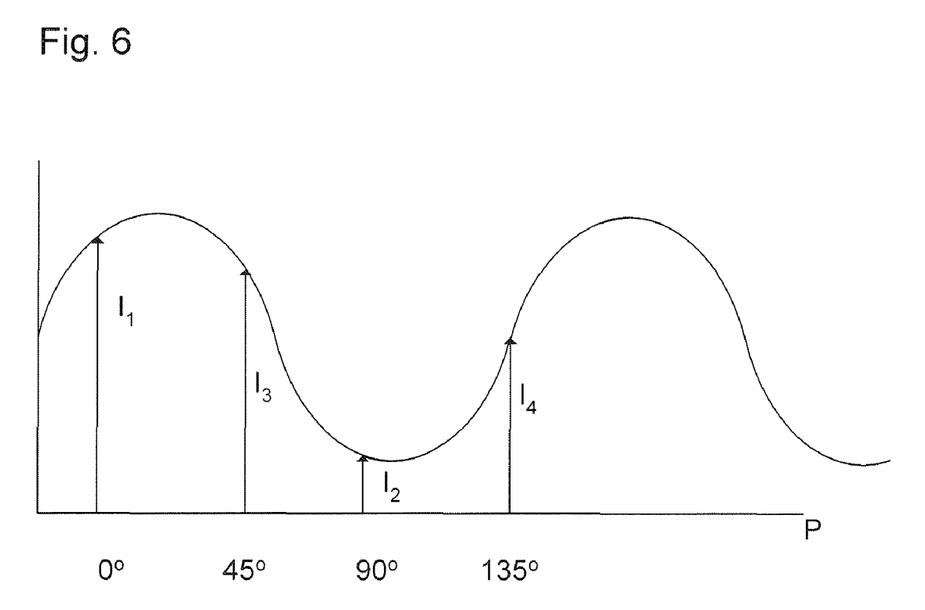
FIG. 6 depicts the relationship between intensity and polarization of a plurality of polarized beams according to an embodiment of the present invention.

The elliptically polarized beam can be reconstructed by a set of four measured intensities as shown in FIG. 6. If the overall intensity, I is given with the following formula:

$$I = 1 + a \cos(2A) + b \sin(2A) \tag{5}$$

wherein the Fourier co-efficient are:

$$a = \left(\frac{I_1 - I_2}{I_1 + I_2}\right) \tag{6}$$

and $$b = \left(\frac{I_3 - I_4}{I_3 + I_4}\right), \tag{7}$$

the elliptically polarized beam is reconstructed for known values of $I_1$, $I_2$, $I_3$ and $I_4$. Applying the relationship of the intensity of the elliptically polarized beam with the amplitude of the individual components (as shown in FIG. 5) gives the amplitudes that can be input into equations (1) and (2) above. The reconstructed beam thereby gives the phase difference ($\Delta$) and relative amplitude alignment (tan $\psi$), thus giving rise to the parameters of the structure 30.

The four pupils are measured on a dedicated CCD camera. These intensities are measured simultaneously so that no measurement time is lost. This opens the possibility of using a pulsed light source such as laser. As there is no phase modulator, the scatterometer of FIG. 7 is essentially independent of the wavelength used. Any errors caused by polarizing beamsplitters are easily calibrated, as they are independent of the angles of incidence and of the azimuthal angles. A benefit of using Wollaston prisms (or other calcite prisms such as Glan-Thompson prisms) is that a high polarization extinction ratio is available across a large wavelength band.

Figure 8:
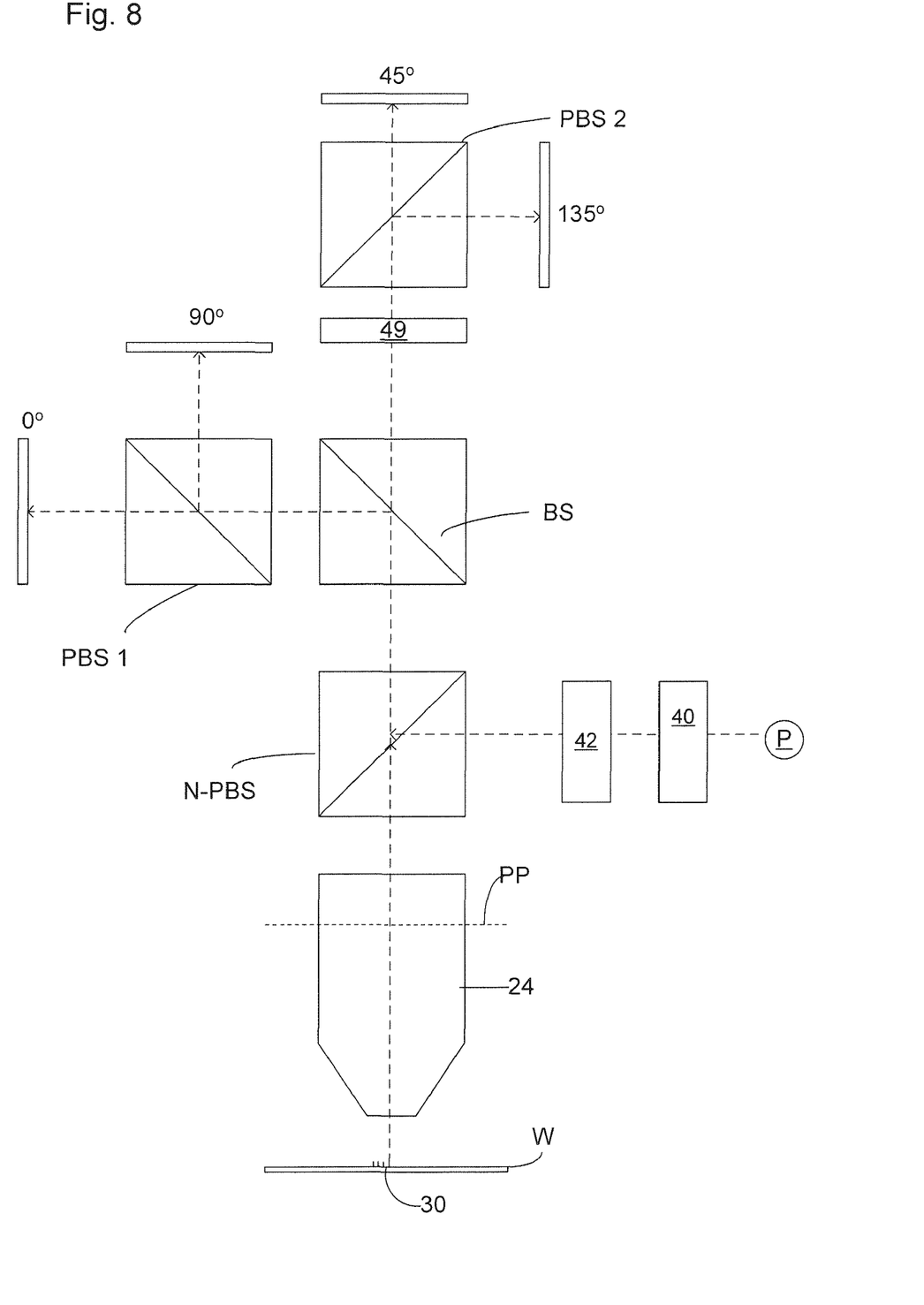
FIG. 8 depicts an ellipsometer according to an embodiment of the present invention.
Figure 9:
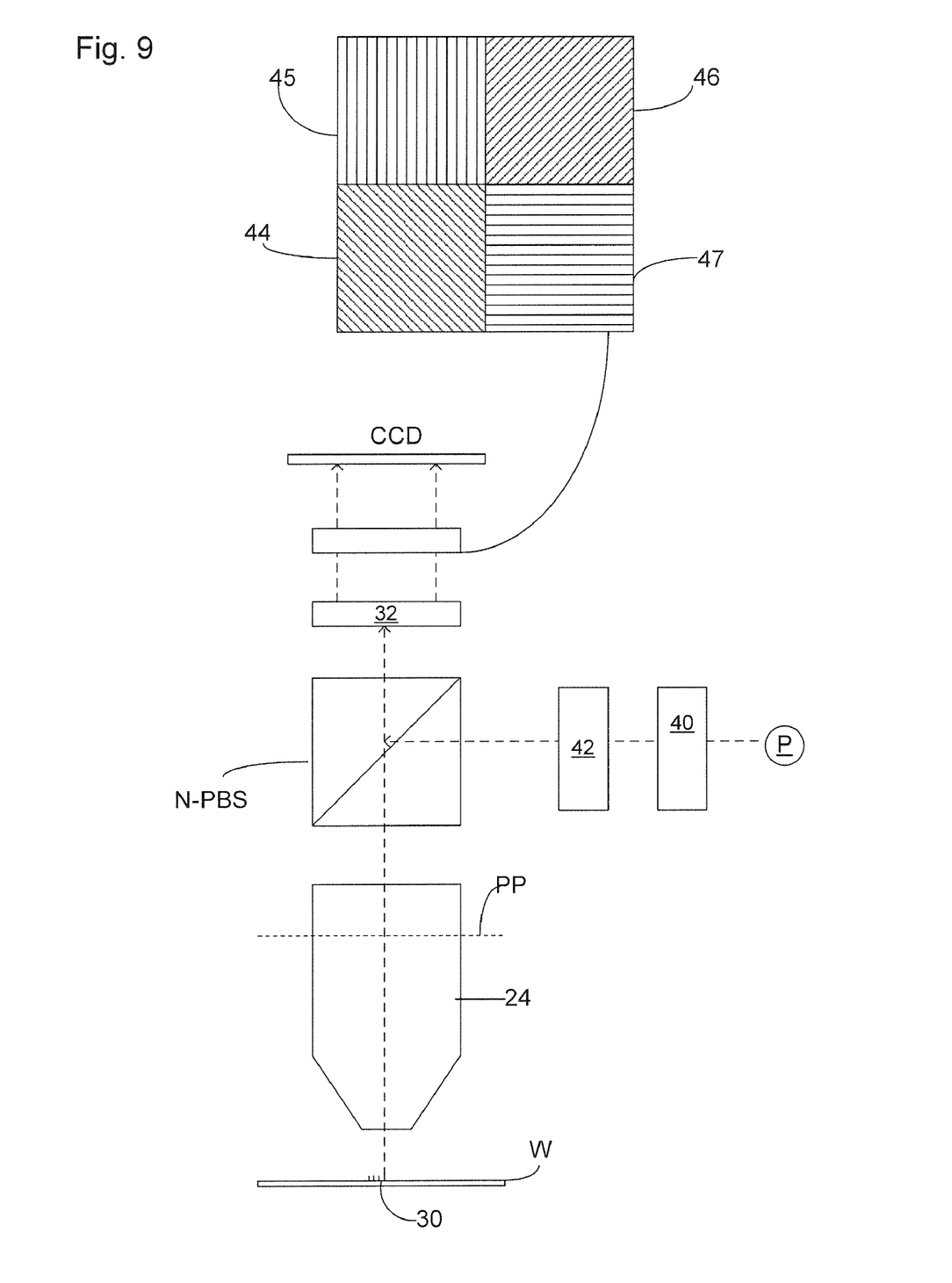
FIG. 9 depicts an ellipsometer according to an embodiment of the present invention.
Figure 10:
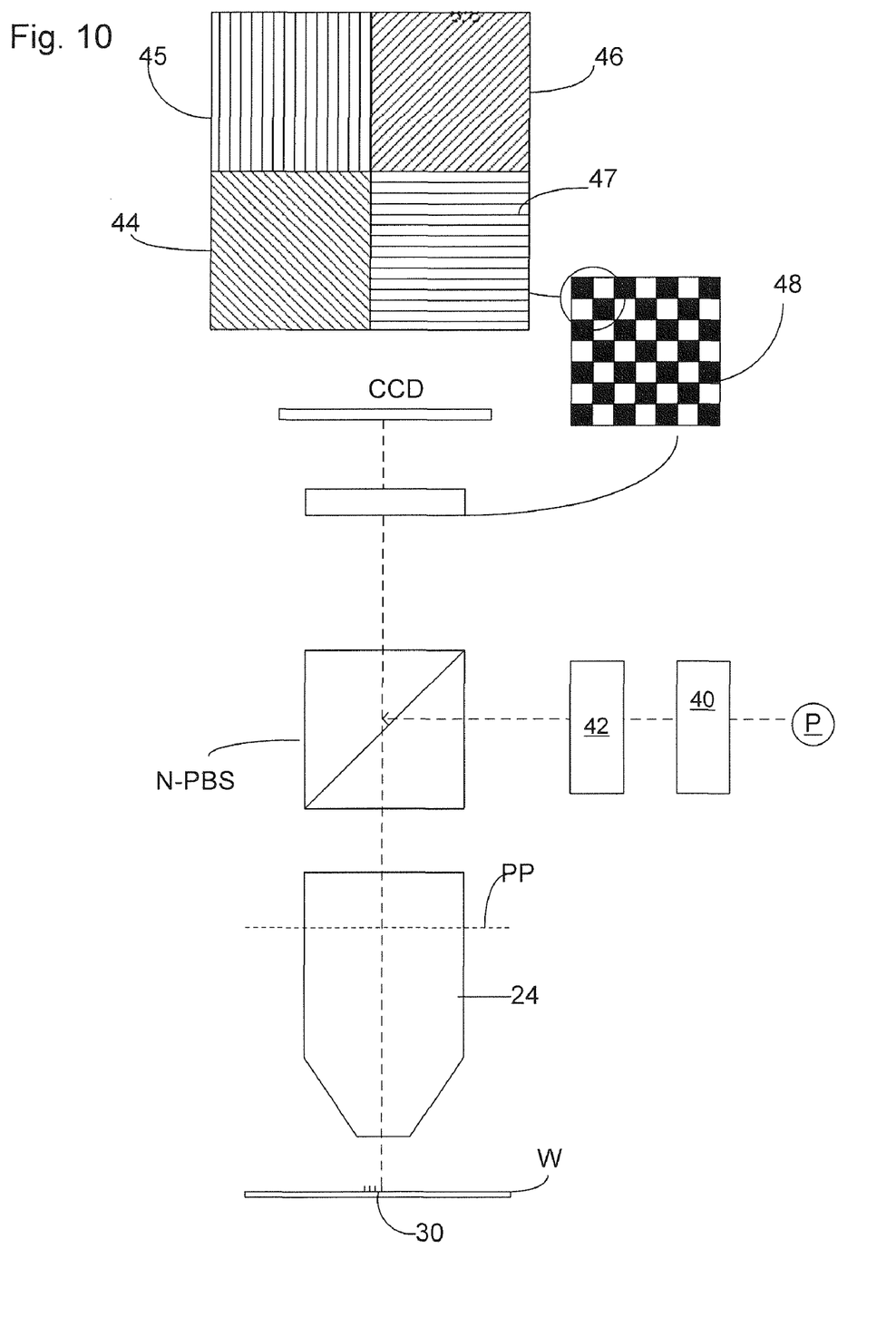
FIG. 10 depicts an ellipsometer according to an embodiment of the present invention.

The apparatus of FIGS. 8-10 may set up with a quarter wave plate in the path of the illumination beam with its main axis oriented at 45 degrees. This results in circular (elliptical) polarization of the illumination beam. Alternatively this quarter wave plate can be left out. This results in linear polarized illumination, which can also have different orientations, but which gives rise to the need of several measurements to ensure that no orientations are missed.

The apparatus of FIGS. 8-10 generate the some four images as the apparatus of FIG. 7 above, and so the intensities $I_1$, $I_2$, $I_3$ and $I_4$ are used for reconstruction of amplitude and phase of original beam in the same way as in the apparatus of FIG. 7. These values are then used in the same way to determine the ellipsometric parameters $\psi$ and $\Delta$. In all of these embodiments, the imaging of the radiation is in the pupil plane: the CCD or camera plane is a conjugate plane of the microscope objective pupil plane. The camera is therefore imaging the pupil plane of the objective. In all of the embodiments, all polarizers are preferably linear polarizers.

FIG. 8 depicts a further embodiment wherein an illumination branch starting at source P transmits a radiation beam through a linear polarizer 40 and a quarter waveplate 42 (i.e. one that is rotated at about 45° with respect to the linear polarizer 40), thus creating circularly polarized light. The light is then incident on a structure 30 to be inspected on the substrate W and then is reflected to a detection branch (shown to be in line with the illumination branch in FIG. 8).

The detection branch propagates the light to a beamsplitter BS, which transmits (approximately) half of the beam as a sub-beam and reflects the other half of the beam as a second sub-beam. The transmitted light from the beamsplitter goes through a half waveplate 49 (rotated by about 22.5° with respect to the linear polarizer, it rotates the incident polarization by about 45 degrees) and on to a polarizing beamsplitter PBS2. Alternatively, the half wave plate could be left out, and the polarizing beam splitter may be rotated by about 45 degrees around its axis. When using different wavelengths, this could have benefits, because a wave plate is mostly optimized for a certain wavelength band.

At the polarizing beamsplitter PBS2, the sub-beam is divided into two separate but optically identical sub-sub-beams with polarizations at about 90° and about 270° respectively. The polarizers have a physical orientation of about 45° and 135° respectively, which gives rise to the above phase shifts of the sub-sub-beams, as polarizers give rise to a phase shift of twice their polarization angle. In other words, the method of rotating one sub-beam is by using a half waveplate, rather than rotating the beamsplitter as in Embodiment one.

The other half of the beam that is reflected in the beamsplitter BS does not go through the half waveplate but it goes immediately to a further polarizing beamsplitter PBS1, half of this beam being transmitted through the polarizing beamsplitter PBS1 and being polarized at about 0°, the other half reflecting off the polarizing beamsplitter PBS1 and thus being polarized at about 90° (thanks to the orthogonal orientations of the polarizers) as shown in FIG. 8.

The sub-sub-beams with their different phase shifts are projected on to four separate camera surfaces. The intensity of each beam is thus measured with respect to its polarization and incident angle and can thus be used to determine the phase difference between the various sub-sub-beams. The overall intensity compared with each individual intensity gives rise to the amplitude and the phase change as discussed in Embodiment one.

FIG. 9 shows an ellipsometer in accordance with embodiment of the present invention. In a scatterometer's illumination branch, circular polarized light is created using a linear polarizer 40 and a quarter wave plate 42 located at about 45° in the same way as in FIG. 8. The light thus polarized from source P propagates via mirrors and lenses and a microscope objective (24 in FIG. 9) towards the structure 30 on the substrate W. The reflected light coming from the substrate W propagates again through the microscope objective 24 towards detection branch of the scatterometer as discussed above. The beam is then physically split using a (e.g. diffractive) optical splitting element 32 into four separate but optically identical sub-beams B. These beams each travel through a differently oriented polarizer and are finally projected on to the camera surface CD. The four polarizers are used as a phase quadrant measurement technique. In other words, quadrant 44 is turned by about 135° with respect to quadrant 45, which is at about 0°. Quadrant 46 is rotated at about 45° with respect to quadrant 45 and quadrant 47 is rotated about 90° with respect to quadrant 45. The intensity of each quadrant is measured independently and combined as described in Embodiment one above.

The benefit of this embodiment is that only one camera CCD is used, reducing hardware and therefore potentially reducing cost and maintenance/calibration requirements.

FIG. 10 shows an ellipsometer in accordance with an embodiment of the invention. The embodiment of FIG. 10 is the same as the embodiment of FIG. 9, except that the beams are not split so that the optical power per field on the camera CCD is not reduced. There is therefore no negative impact on throughput or on camera integration time.

The way this is done is that a matrix of polarizers 48 creates an array of units, each unit having four quadrants, each quadrant having different polarizer orientations as described in the embodiment thereof FIG. 9. In other words, each unit in the matrix includes a first quadrant 45 with about a 0° polarization, a second quadrant 46 with about a 45° polarization, a third quadrant 47 with about a 90° polarization, and a fourth quadrant 44 with about a 135° polarization with respect to the first quadrant 45. As mentioned above, polarization orientations of the polarizers gives rise to a phase shift of the radiation beam of twice the orientation angle.

Each of the units in the matrix is detected by a camera (software may be used to separate the different units after detection) and the relative intensities of the different quadrants gives an indication of the relative amplitudes and phase differences as discussed earlier. The polarization state of the reflected beam may therefore be determined and the structure's effect on the beam gives rise to the properties of the structure through reverse engineering.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. An inspection apparatus configured to measure a property of a substrate, the inspection apparatus comprising:
   a light source configured to supply a radiation beam;
   an optical element configured to focus the radiation beam onto a surface of the substrate;
   a beamsplitter configured to separate the radiation beam once reflected from the surface of the substrate into first and second orthogonally polarized sub-beams;
   a first polarizing beamsplitter configured to split the first sub-beam into two sub-sub-beams with about 0 and 90 degree polarization respectively;
   a second polarizing beamsplitter rotated by about 45 degrees with respect to the first polarizing beamsplitter and configured to split the second sub-beam into two sub-sub-beams with about 45 and 135 degree polarization respectively; and
   a detector system configured to detect simultaneously an angle-resolved spectrum of all four sub-sub-beams reflected from the surface of the substrate.

2. The inspection apparatus according to claim 1, wherein the radiation beam reflected from the substrate is elliptically polarized.

3. The inspection apparatus according to claim 1, further comprising an optical wedge configured to deflect the sub-sub-beams onto the detector system.

4. The inspection apparatus according to claim 1, further comprising a deflector configured to deflect the sub-sub-beams onto the detector system.

5. The inspection apparatus according to claim 1, wherein the beamsplitter and the first and second polarizing beamsplitters comprise polarizing prisms.

6. The inspection apparatus according to claim 1, wherein the beamsplitter and the first and second polarizing beamsplitters comprise Wollaston prisms.

7. The inspection apparatus according to claim 1, wherein the sub-beams comprise a TE-beam and a TM-beam.

8. The inspection apparatus according to claim 1, further comprising a focussing system and an optical wedge placed in the image plane of the focussing system configured to redirect the polarized sub-sub-beams in different directions such that the sub-sub-beams are received at different positions on the detector.

* * * * *

UNITED STATES PATENT AND TRADEMARK OFFICE
CERTIFICATE OF CORRECTION

PATENT NO. : 7,839,506 B2  Page 1 of 1
APPLICATION NO. : 12/718599
DATED : November 23, 2010
INVENTOR(S) : Straaijer et al.

It is certified that error appears in the above-identified patent and that said Letters Patent is hereby corrected as shown below:

Column 16, line 39, claim 8, delete "arereceived" and replace with "are received".

Signed and Sealed this
Twenty-second Day of February, 2011

David J. Kappos
*Director of the United States Patent and Trademark Office*